US010888340B2

(12) United States Patent
Awtrey et al.

(10) Patent No.: US 10,888,340 B2
(45) Date of Patent: Jan. 12, 2021

(54) METHOD AND CUT GUIDE FOR BIPLANAR WEDGE OSTEOTOMY

(71) Applicant: Wright Medical Technology, Inc., Memphis, TN (US)

(72) Inventors: George Matthew Awtrey, Bartlett, TN (US); Vinay D. Patel, Memphis, TN (US); Scott A. Armacost, Germantown, TN (US); Mary McCombs-Stearnes, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 300 days.

(21) Appl. No.: 16/036,980

(22) Filed: Jul. 17, 2018

(65) Prior Publication Data

US 2018/0317942 A1    Nov. 8, 2018

Related U.S. Application Data

(63) Continuation of application No. 14/842,944, filed on Sep. 2, 2015, now Pat. No. 10,039,559.

(51) Int. Cl.
*A61B 17/15* (2006.01)
*A61B 17/17* (2006.01)
(Continued)

(52) U.S. Cl.
CPC .......... *A61B 17/1796* (2013.01); *A61B 6/485* (2013.01); *A61B 17/152* (2013.01);
(Continued)

(58) Field of Classification Search
CPC .................. A61B 17/15–152; A61B 17/1775
See application file for complete search history.

(56) References Cited

U.S. PATENT DOCUMENTS 5,540,695 A    7/1996  Levy
5,601,565 A *  2/1997  Huebner ................ A61B 17/15
                                                 606/79
(Continued)

FOREIGN PATENT DOCUMENTS

CN       102781348 A      11/2012
EP         2092899 A2      8/2009
(Continued)

OTHER PUBLICATIONS

Examination Report No. 2 issued in connection with corresponding Australian Patent Application No. 2018204463, dated Jun. 28, 2019, 8 pages.

(Continued)

*Primary Examiner* — Zade Coley
(74) *Attorney, Agent, or Firm* — Duane Morris LLP

(57) ABSTRACT

A wedge osteotomy method inserts a first wire into a first bone of the foot, distal from tissue to be removed. A second wire is inserted into a second bone, so the tissue to be removed is distal from the second wire. A cut guide is pivoted about the first wire, until a first axis of the cut guide is parallel with a longitudinal axis of the first metatarsal. The cut guide has a slot perpendicular to the first axis for guiding a cutter to cut bone, while the first axis is aligned with the longitudinal axis of the first metatarsal. The cut guide is then pivoted about the second wire, until the first axis is aligned with the longitudinal axis of the talus, and bone is cut through the slot, to form a second planar cut into or through bone material.

10 Claims, 15 Drawing Sheets

(51) Int. Cl.
*A61B 17/16* (2006.01)
*A61B 6/00* (2006.01)
A61B 90/00 (2016.01)
A61B 17/80 (2006.01)

(52) U.S. Cl.
CPC ...... *A61B 17/1682* (2013.01); *A61B 17/1703* (2013.01); *A61B 17/1775* (2016.11); *A61B 17/8061* (2013.01); *A61B 17/8095* (2013.01); *A61B 2090/3966* (2016.02)

(56) References Cited

U.S. PATENT DOCUMENTS

| | | | |
|---|---|---|---|
| 5,676,668 A | 10/1997 | McCue et al. | |
| 5,722,978 A | 3/1998 | Jenkins, Jr. | |
| 5,843,085 A | 12/1998 | Graser | |
| 7,083,624 B2 | 8/2006 | Irving | |
| 8,083,746 B2 * | 12/2011 | Novak | A61B 17/152 606/88 |
| 8,182,489 B2 | 5/2012 | Horacek | |
| 8,496,662 B2 | 7/2013 | Novak et al. | |
| 8,784,498 B2 | 7/2014 | Scheland | |
| 8,888,785 B2 | 11/2014 | Kmmann et al. | |
| 9,005,207 B2 | 4/2015 | Dodds et al. | |
| 9,060,822 B2 | 6/2015 | Lewis et al. | |
| 9,492,183 B2 | 11/2016 | Wilkinson et al. | |
| 2005/0273112 A1 * | 12/2005 | McNamara | A61B 17/15 606/87 |
| 2007/0233138 A1 | 10/2007 | Figueroa et al. | |
| 2007/0233145 A1 | 10/2007 | Richardson et al. | |
| 2010/0217328 A1 * | 8/2010 | Terrill | A61B 17/8061 606/286 |
| 2010/0256638 A1 * | 10/2010 | Tyber | A61B 17/1717 606/62 |
| 2011/0172672 A1 | 7/2011 | Dubeau et al. | |
| 2011/0218540 A1 * | 9/2011 | Ammann | A61B 17/68 606/87 |
| 2013/0204261 A1 | 8/2013 | Eschle et al. | |
| 2014/0180341 A1 | 6/2014 | Kang et al. | |

FOREIGN PATENT DOCUMENTS

| | | |
|---|---|---|
| FR | 2790380 A1 | 9/2000 |
| JP | 200729657 A | 2/2007 |
| JP | 2013540012 A | 10/2013 |
| WO | 2003063682 A2 | 8/2003 |
| WO | 2010025183 A1 | 3/2010 |
| WO | 2011063281 A1 | 5/2011 |
| WO | 2012106477 A1 | 8/2012 |
| WO | 2015003284 A2 | 7/2014 |
| WO | 2014152535 A1 | 9/2014 |
| WO | 2015105880 A1 | 7/2015 |

OTHER PUBLICATIONS

Second Office Action issued in connection with corresponding Chinese Patent Application No. 201610170261.7, dated Jun. 13, 2019, 6 pages.
Sammarco, V.J. et al., "Midtarsal Arthrodesis in the Treatment of Charcot Midfoot Arthropathy", J. Bone Joint Surg Am., Jan. 2009, 91:80-91.
Grant, W.P. et al., "A Retrospective Analysis of 50 Consecutive Charcot Diabetic Salvage Reconstructions", The Journal of Foot & Ankle Surgery, Jan./Feb. 2009, 48(1):30-308.
Assal, M. et al., "Realignment and Extended Fusion with Use of a Medial Column Screw for Midfoot Deformities Secondary to Diabetic Neuropathy: Surgical Technique", J Bone Joint Surg Am., Mar. 2010, 92:20-31.
Scott, Ryan T., et al., "Osteotomies for the Management of Charcot Neuroarthropathy of the Foot and Ankle", Clin Podiatr Med Surg, Jul. 2015, 32(3):405-418.
McAlister, J.E. and Philbin, T. M., "A Closer Look At the Distal Tibial Osteotomy for Ankle Varus", Podiatry Today, Oct. 29, 2012, 25(11)1-4.
European Search Report and Search Opinion issued for corresponding European patent application No. 16161879.8, dated Jan. 18, 2017, 7 pages.
Office Action issued for corresponding Canadian patent application No. 2,924,441, dated Mar. 28, 2017, 3 pages.
Zhou, Y. et al. "A Prospective Study of Midfoot Osteotomy Combined with Adjacent Joint Sparing Internal Fixation in Treatment of Rigid Pes Cavus Deformity", Journal of Orthopaedic Surgery and Research, Jun. 2014, 9:44, pp. 1-5.
Salvation 3Di Plating System Surgical Technique, pp. 1-20, [retrieved from Internet on Apr. 24, 2017] <URL: http://www.wmtemedia.com/ProductFiles/Files/PDFs/009722_EN_LR_LE_pdf>.
Examination Report No. 1 issued for corresponding Australian patent application No. 2016201813, dated Apr. 24, 2017, 10 pages.
Office Action issued in corresponding Japanese patent application No. 2016-058237, dated Jun. 27, 2017, 2 pages.
Office Action issued in connection with corresponding Canadian patent application No. 2,924,441, dated Dec. 11, 2017 5 pages.
Office Action issued in connection with corresponding European patent application No. 16161879.8, dated Mar. 26, 2018, 5 pages.
Examination Report No. 2 issued for corresponding Australian patent application No. 2016201813, dated Aug. 29, 2017, 4 pages.
Examination Report No. 1 issued in connection with corresponding Australian Patent Application No. 2020200968, dated Jul. 17, 2020, 4 pages.
First Office Action issued in connection with corresponding Canadian Patent Application No. 3,033,607, dated Feb. 3, 2020, 5 pages.
Office Action issued in corresponding Chinese Patent Application No. 201610170261.7, dated Aug. 2, 2018, 6 pages.

* cited by examiner

METHOD AND CUT GUIDE FOR BIPLANAR WEDGE OSTEOTOMY

This application is a continuation of U.S. patent application Ser. No. 14/842,944, filed on Sep. 2, 2015, the entirety of which is herein incorporated by reference.

FIELD

This disclosure relates generally to medical devices, and more specifically to devices and methods for a biplanar wedge osteotomy.

BACKGROUND

Patients with Charcot neuropathy may experience swelling, and joint subluxation (dislocation). Eventually, the mal-positioning of the joints can result in a bony prominence beneath the foot. Patients with neuropathy may not experience pain, and may continue to walk and bear weight on the affected foot. If left untreated, ulceration and infection may result. Treatment goals include allowing the ulcers to heal, creating a plantagrade foot, and preventing infection.

"Meary's angle" is one measure of the deformity of the foot. Meary's angle is the angle between the central longitudinal axis of the talus and the central longitudinal axis of the first metatarsal, as viewed in a vertical (parasagittal) plane. In a normal foot, Meary's angle is 0 degrees. In the case of a Charcot foot, Meary's angle can reach 15-30 degrees or more.

To eliminate the bony prominence and restore the arch in patients with severe Charcot deformity affecting multiple foot joints, surgeons have performed a biplanar wedge osteotomy. In this procedure, the surgeon removes a biplanar wedge of bone from the plantar side of the foot. By rejoining the remaining bones, the surgeon is able to restore the foot into a stable plantagrade foot that can fit in a shoe and can support activity with proper bracing. Thus, the surgeon tries to reduce Meary's angle to approximately zero (i.e., between zero and four degrees).

SUMMARY

In some embodiments, a method for bi-planar wedge osteotomy of a foot comprises the steps of: (a) inserting a first wire at least into a first bone of the foot, so that the first wire is distal from tissue to be removed; (b) inserting a second wire into a second bone of the foot, so that the tissue to be removed is distal from the second wire; (c) pivoting a cut guide about the first wire, until a first axis of the cut guide is parallel with a longitudinal axis of a first metatarsal of the foot, the cut guide having a slot perpendicular to the first axis of the cut guide for guiding a cutter; (d) cutting bone through the slot while the first axis of the cut guide is aligned with the longitudinal axis of the first metatarsal; (e) pivoting the cut guide about the second wire, until the first axis of the cut guide is aligned with the longitudinal axis of the talus; and (f) cutting bone through the slot while the first axis of the cut guide is aligned with the longitudinal axis of the talus, to form a second planar cut into or through bone material.

In some embodiments, a method for bi-planar wedge osteotomy of a foot comprises the steps of: inserting a first wire at least into a first bone of the foot, so that the first wire is distal from tissue to be removed; inserting a second wire into a second bone of the foot, so that the tissue to be removed is distal from the second wire; pivoting a cut guide about the first wire, until a first axis of the cut guide is parallel with a longitudinal axis of a first metatarsal of the foot, the cut guide having a slot perpendicular to the first axis of the cut guide for guiding a cutter; inserting a third wire through the cut guide, so as to fix the cut guide to the first bone while the first axis of the cut guide is aligned with the longitudinal axis of the first metatarsal; cutting bone through the slot while the cut guide is fixed by the first and third wires, to form a first planar cut into or through bone material; pivoting the cut guide about the second wire, until the first axis of the cut guide is aligned with the longitudinal axis of the talus; inserting a fourth wire through the cut guide, so as to fix the cut guide to the second bone while the first axis of the cut guide is aligned with the longitudinal axis of the talus; and cutting bone through the slot while the cut guide is fixed by the second and fourth wires, to form a second planar cut into or through bone material.

In some embodiments, a cut guide comprises a body having a first face, a second face opposite the first face, and a straight slot therethrough for guiding a blade, the slot extending from the first face to the second face. The body has a row of holes extending therethrough from the first face to the second face, the row of holes being parallel to the slot. The body has an alignment opening extending parallel to the first face, the alignment opening perpendicular to the slot, the alignment opening configured to receive a radiopaque member therethrough.

DETAILED DESCRIPTION

Figure 1:
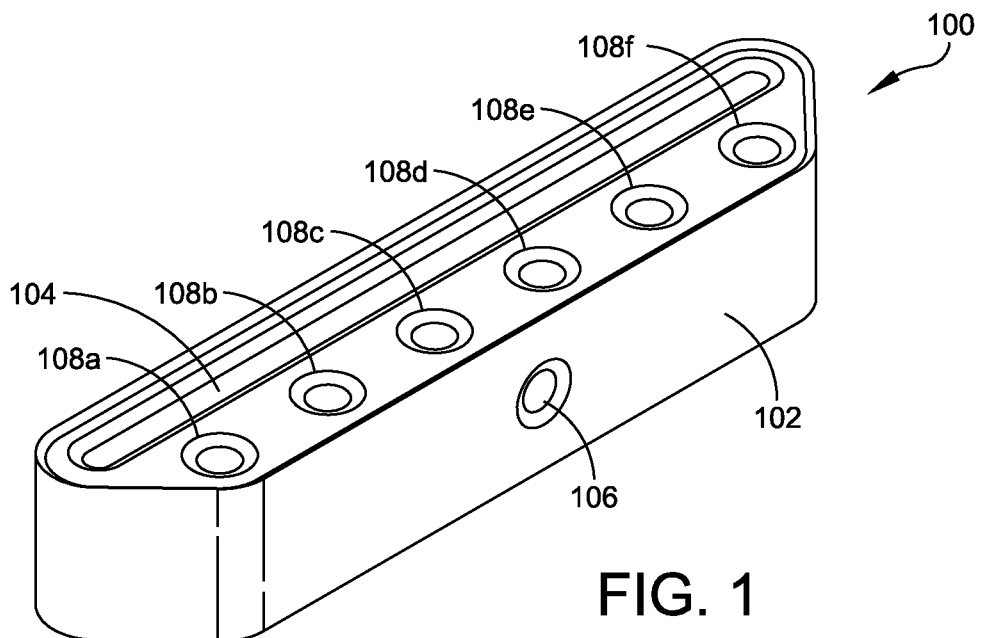
FIG. 1 is an isometric view of a cut guide according to some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Unless otherwise indicated, like reference numerals in different drawings indicate like structures.

This disclosure provides a cut guide and a method of using the cut guide, for a compound angle osteotomy, such as a biplanar medial column osteotomy. The method and cut guide enable a surgeon to consistently align the two planar cuts of the foot bones to restore a plantigrade structure and substantially reduce Meary's angle.

Figure 2:
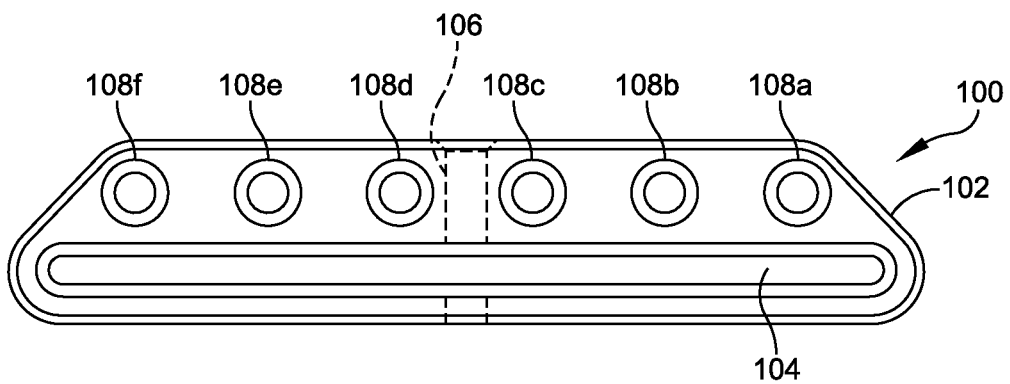
FIG. 2 is a plan view of the cut guide of FIG. 1.
Figure 3:
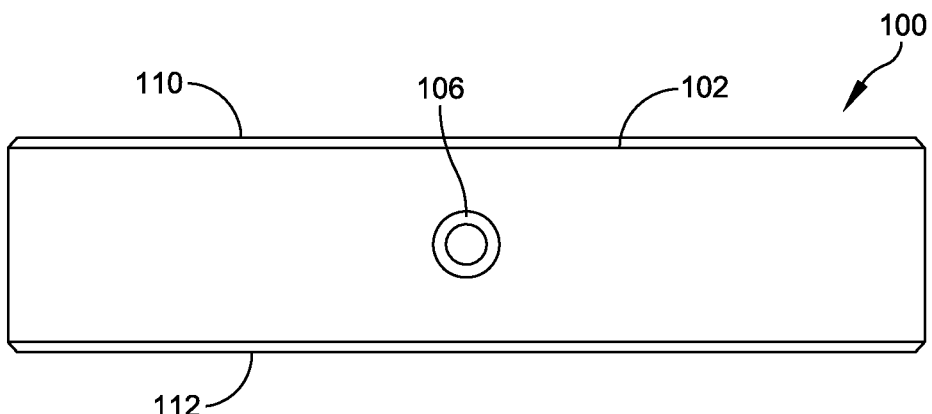
FIG. 3 is a side elevation view of the cut guide of FIG. 2.

FIGS. 1-3 show an exemplary embodiment of a cut guide 100. The cut guide 100 comprises a body 102 having a first face 110 and a second face 112 opposite the first face 110. In some embodiments, the body 102 has a generally trapezoidal shape in plan view. In other embodiments, the body has a generally rectangular shape in plan view. In some embodiments, the body 102 has a rectangular cross section, and optionally has rounded corners. The body 102 has a straight slot 104 therethrough for guiding a blade 240 (shown in FIG. 7). The slot 104 extends from the first face 110 to the second face 112. In some embodiments, the slot 104 is as long as the largest expected cut from a dorsal side of a patient's foot to a plantar side of the foot. For example, slot 104 can have a length of about 5 cm (2 inches). In some embodiments, the slot 104 extends nearly the entire length of the body 102. For example, in some embodiments, the length of the body is about 0.5 cm (0.2 inch) longer than the slot 104. In other embodiments, the slot 104 only extends part of the length of the body 102.

The body 102 has a row of holes 108a-108f extending therethrough from the first face 110 to the second face 112. The row of holes 108a-108f is parallel to the slot 104. The holes 108a-108f can be sized to receive wires or pins to be used during a surgical procedure, such as a 2.4 mm k-wire. In some embodiments, six holes 108a-108f are provided at evenly spaced intervals. Other embodiments can include any integer number of holes greater than or equal to two. Providing more than two holes allows the surgeon flexibility to locate healthy bone into which he/she can insert a k-wire securely for fixing the cut guide in the proper orientation to make the cuts for the wedge osteotomy.

In some embodiments, the body 102 has an alignment opening 106 extending parallel to the first face 110. A first axis 109 of the cut guide coincides with the central longitudinal axis of the alignment opening 106. The alignment opening 106 is perpendicular to the slot 102. The alignment opening 106 is configured to receive a radiopaque member therethrough. For example, the radiopaque member can be made of a metal, such as stainless steel. In some embodiments, the alignment opening 106 is a smooth through-hole for receiving a k-wire.

In other embodiments (not shown), the alignment opening 106 is threaded, to receive a threaded member. In other embodiments (not shown), instead of the alignment opening 104, the body has a unitary elongated alignment member projecting outward from the body; for example, the entire body, including the alignment member, can be made of a radiopaque material.

In some embodiments, the cut guide 100 is made of stainless steel, such as an ASTM A564-630 steel.

Figure 4:
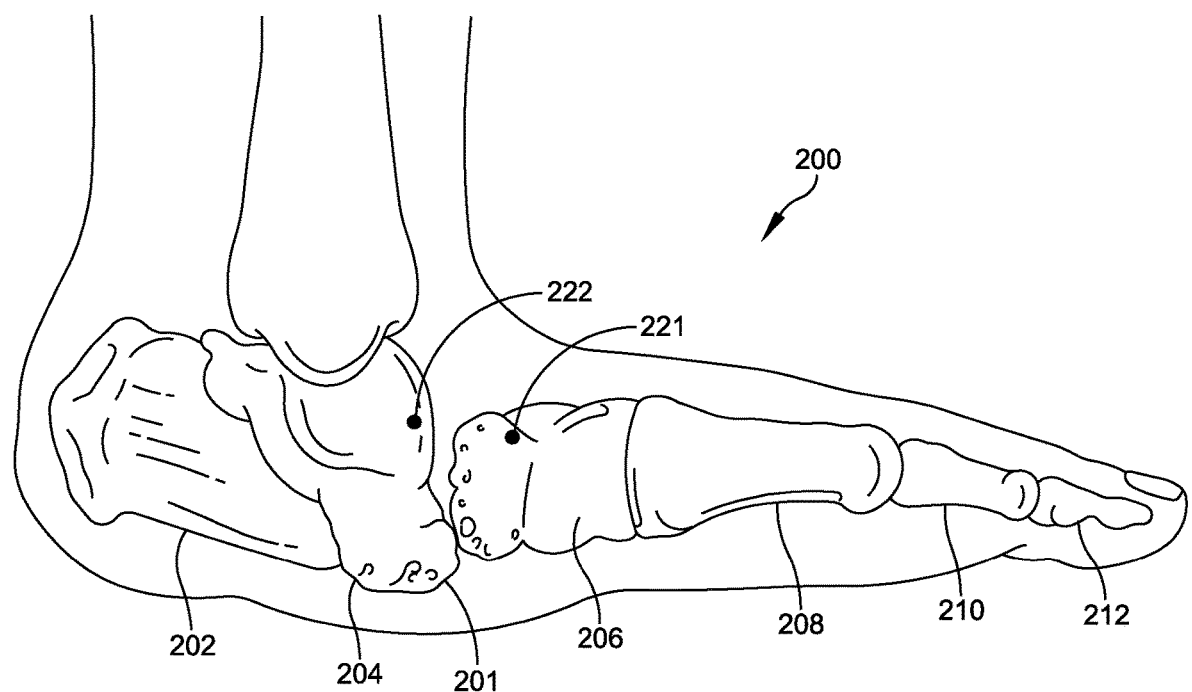
FIG. 4 is a schematic medial view showing the skeletal structure of a foot with Charcot disease induced deformity.

FIG. 4 shows an example of a Charcot foot 200 having a bony prominence 201 resulting in a convex foot bottom that is susceptible to ulceration. FIG. 4 is a medial view, showing the calcaneus 202, talus 204, cuneiform 206, first metatarsal 208, phalange 210 and distal phalange 212.

FIG. 4 also shows a first wire (e.g., k-wire) 221 and a second wire (e.g., k-wire) 222 inserted by the surgeon. The first wire 221 and the second wire 222 are inserted in one or more of the group consisting of the first metatarsal 208, a cuneiform 206, a navicular, and the talus 204. The surgeon selects the location of the first wire 221 and second wire 222 based largely on three factors. First, the surgeon selects locations having healthy bone, on opposite sides (in the proximal-distal direction) of the tissue to be removed. The surgeon inserts the first wire 221 at least into a first bone (e.g., 206) of the foot, so that the first wire 221 is distal from tissue to be removed. The surgeon inserts a second wire 222 into a second bone (e.g., 204) of the foot, so that the tissue to be removed is distal from the second wire. In some embodiments, the first bone is the navicular, cuneiform, or first metatarsal, and the second bone is the talus, navicular or cuneiform. The positioning of these wires is discussed with reference to FIG. 7.

Figure 7:
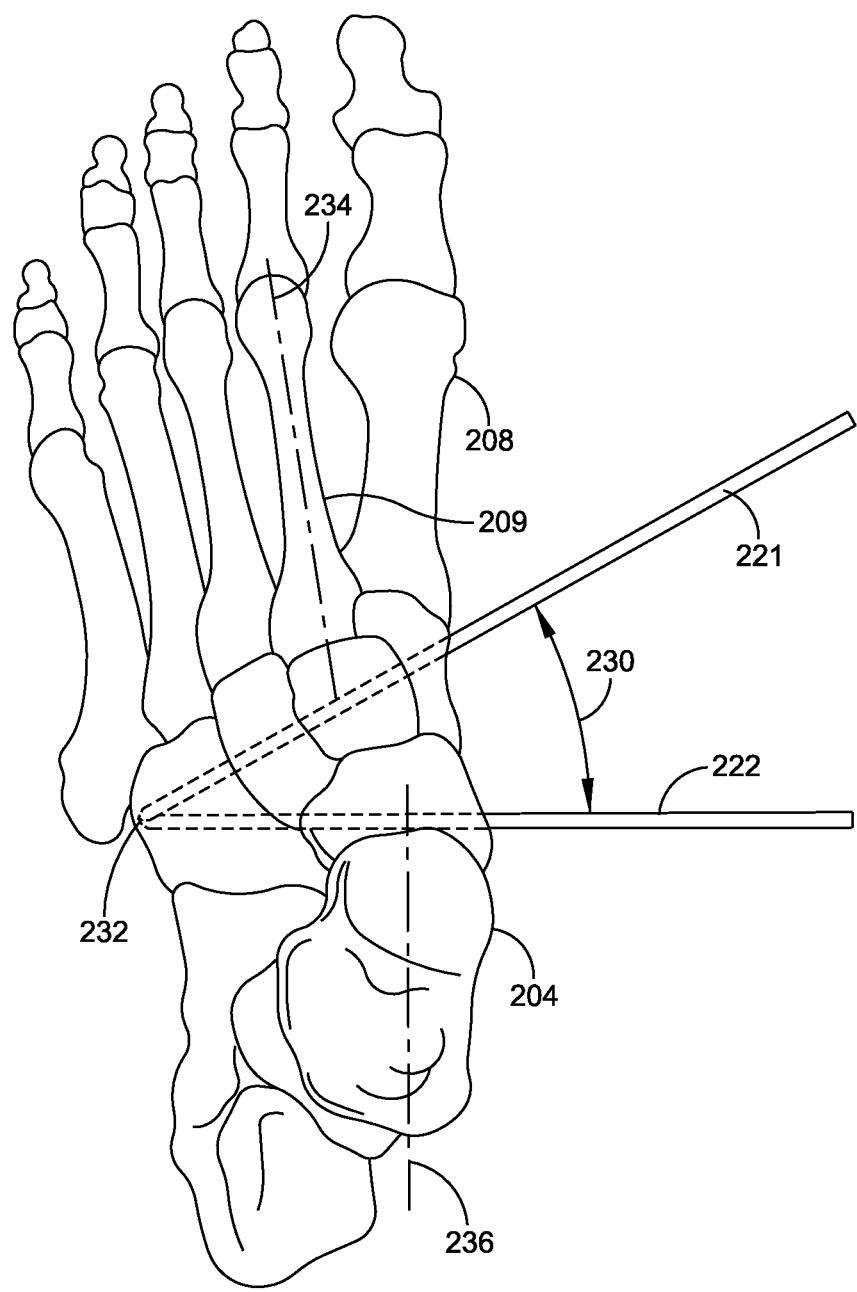
FIG. 7 is a superior view of the foot of FIG. 6, with the first and second wires positioned.

When viewed from the superior view, as shown in FIG. 7, the tissue to be removed is within a triangular region bounded by the first 221 and second wire 222. The surgeon also decides where the apex 232 (also referred to as the vertex) of the wedge is to be located. The apex 232 can be located at the edge of the foot 200 opposite the edge from which the wires 221, 222 are inserted, for cutting completely across the foot 200 and realigning distal foot bones relative to the talus 204. For example, in a procedure with a medial approach, the apex 232 can be at the lateral edge of the foot 200. If the surgeon can remove all the diseased bone with a wedge having an apex 232 that does not extend beyond the edge of the foot, the surgeon will do so (so as to remove the smallest wedge that contains all the diseased bone). If the diseased tissue extends far in the proximal-distal direction, the surgeon may choose to remove a larger wedge, and the surgeon can select an apex 232 which is beyond the lateral edge of the foot.

In a normal foot, the longitudinal axis 234 of the 2nd metatarsal 209 is in line with the longitudinal axis 236 off the talus, when viewed in the superior view. The example of FIG. 7 shows a misalignment between the axes 234 and 236, to be corrected by the angle 230 between the first and second wire. Thus, in some embodiments, the surgeon selects the angle 230 of the wedge that will bring the central longitudinal axis 234 of the second metatarsal 209 in line with the axis 236 of the talus 204, in the superior view, and then chooses an apex 232 that provides the minimum size of the triangular region between the first wire 221 and second wire 222 sufficient to remove the diseased bone (i.e., minimizes the distance beyond the lateral edge of the foot to the apex 232). In selecting the locations of the first wire 221 and the second wire 222, the surgeon takes into account the distance between the row of holes 108a-108f and the slot 104 in the cut guide 100, to ensure that a cut made using the cut guide 100 is entirely in good bone.

In some embodiments, the first wire 221 is positioned, so a projection of the first wire 221 in a transverse plane of the foot is approximately perpendicular to a longitudinal axis 234 of a second metatarsal 209 of the foot 200. In some embodiments, a projection of the second wire 222 in the transverse plane is approximately perpendicular to a longitudinal axis 236 of a talus 204.

FIGS. 5-17 show a method for bi-planar wedge osteotomy of the foot 200. The example of FIGS. 5-17 shows a biplanar medial wedge osteotomy using a medial approach. In other examples, the method can be used for medial or lateral osteotomies, and for medial or lateral approach.

Figure 5:
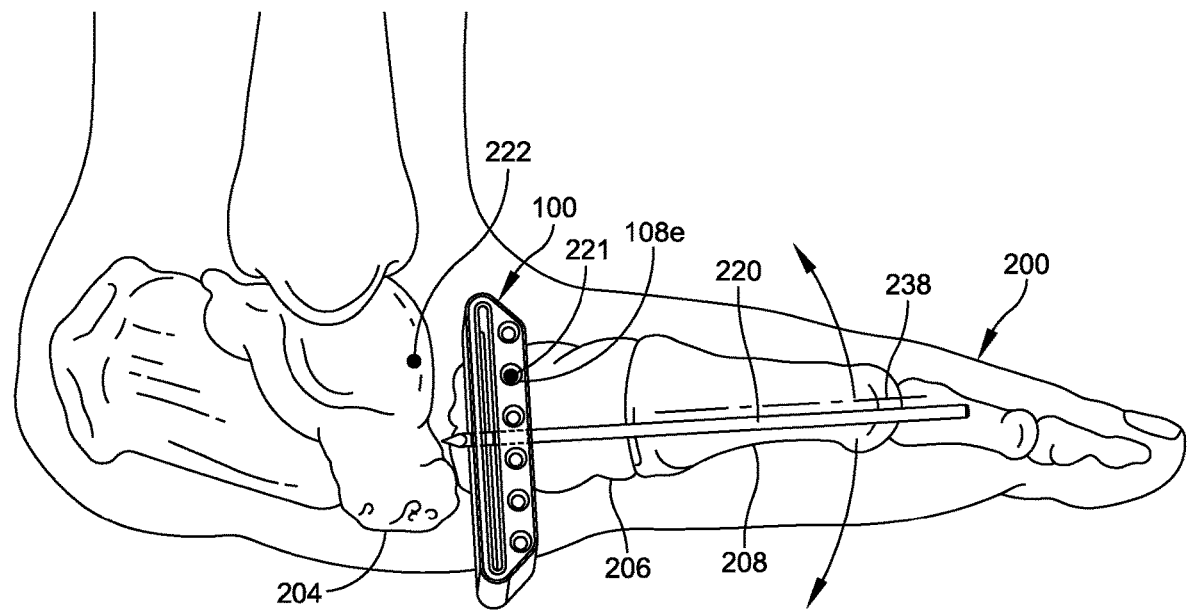
FIG. 5 shows pivoting and alignment of the cut guide of FIG. 1 on the distal portion of the foot of FIG. 4.

As shown in FIG. 5, the surgeon places one of the holes 108a-108f over the first wire 221, inserting the first wire through a first hole in the cut guide with the slot 104 located between the wire 221 and the diseased tissue.

The surgeon inserts a straight elongated member 220 through the alignment opening 106 extending through the cut guide 100. Since the alignment opening 106 is perpendicular to the slot 104, the elongated member 220 is perpendicular to the slot 104 following insertion. Because of its length, the elongated member 220 makes it easy to detect whether the cut guide deviates from alignment parallel to the longitudinal axis of the first metatarsal (when making the first cut) or the talus (when making the second cut). The elongated member 220 is external to the foot 200 at all times during the procedure.

The surgeon pivots the cut guide 100 about the first wire 221, until a first axis 109 of the cut guide (coinciding with the longitudinal axis of the alignment opening 106 and the longitudinal axis of the elongated member 220) is parallel with a longitudinal axis 238 of the first metatarsal 208 of the foot 200. Since the slot 104 of the cut guide 100 is perpendicular to the first axis 109 of the cut guide, the step of aligning the elongated member 220 with the longitudinal axis of the first metatarsal 208 orients the slot 104 perpendicular to the longitudinal axis 238 of the first metatarsal 208 for guiding a cutter 240.

In some embodiments, the elongated member 220 is radiopaque, and the surgeon views the first metatarsal 208 and the elongated member 220 by fluoroscopy while aligning the elongated member 220 with the longitudinal axis of the first metatarsal 238. In some embodiments, the elongated metal member slidably or threadably engages the alignment opening. For example, the elongated member 220 can be a stainless steel k-wire.

Figure 6:
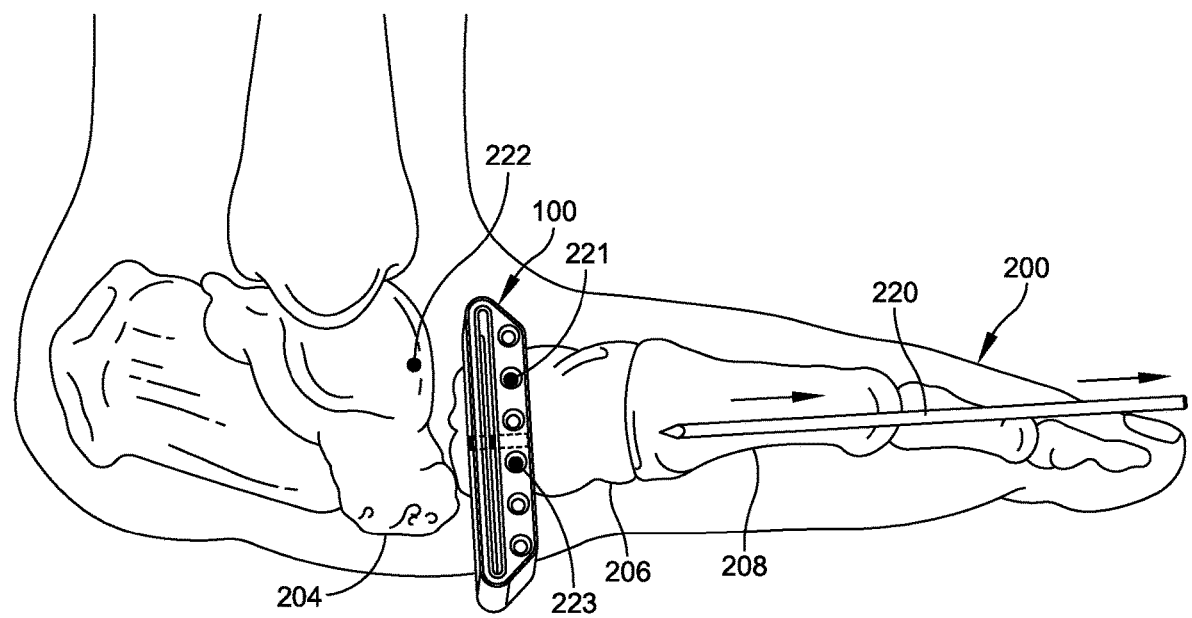
FIG. 6 shows fixation of the cut guide to the distal portion of the foot.

FIG. 6 shows a step of inserting a third wire 223 through the cut guide 100, so as to fix the cut guide to the first bone 206 while the first axis 109 of the cut guide 100 is aligned with the longitudinal axis 238 of the first metatarsal 208. The third wire 223 can be inserted in any of the holes 108a-108f other than the hole through which wire 221 is inserted. The location of wire 223 is selected so that wire 223 is fixed in healthy bone. Once the third wire 223 is inserted and the cut guide location and orientation are fixed, the elongated member 220 can be removed as shown.

Figure 8:
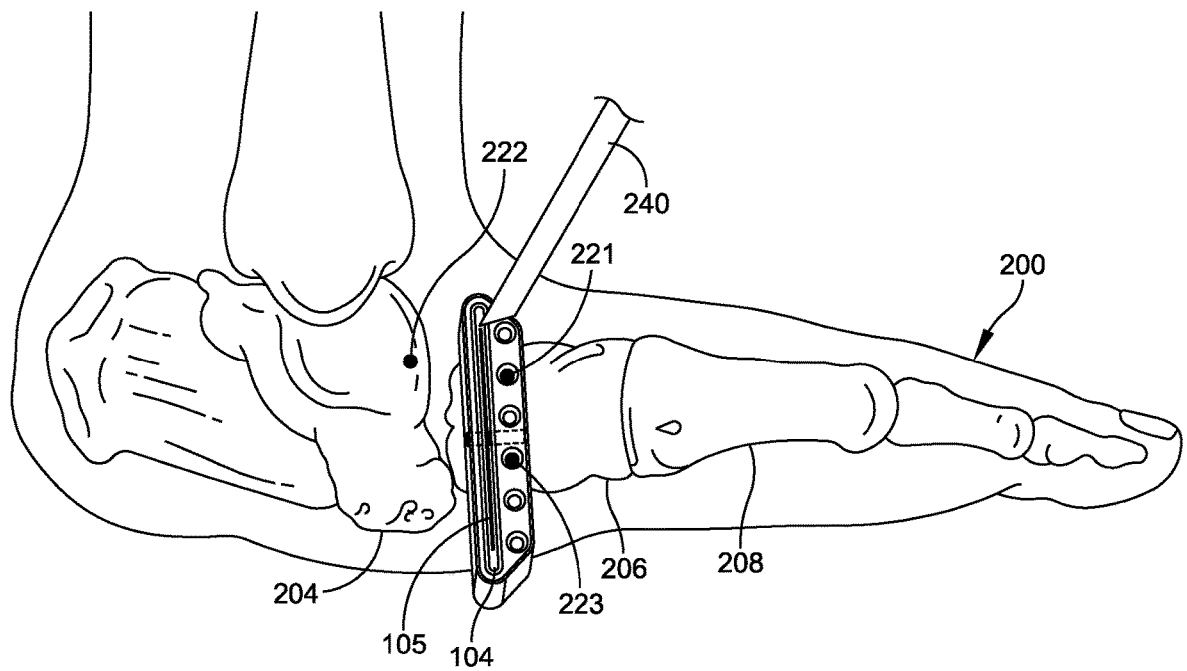
FIG. 8 shows a saw blade cutting a first bone using the cut guide.

As shown in FIG. 8, the surgeon cuts bone 206 through the slot 104 using the cutter 240 while the cut guide 100 is fixed by the first wire 221 and third wire 223, to form a first planar cut 105 into or through bone material. In the example of FIG. 8, the surgeon cuts completely through the bone material.

Figure 9:
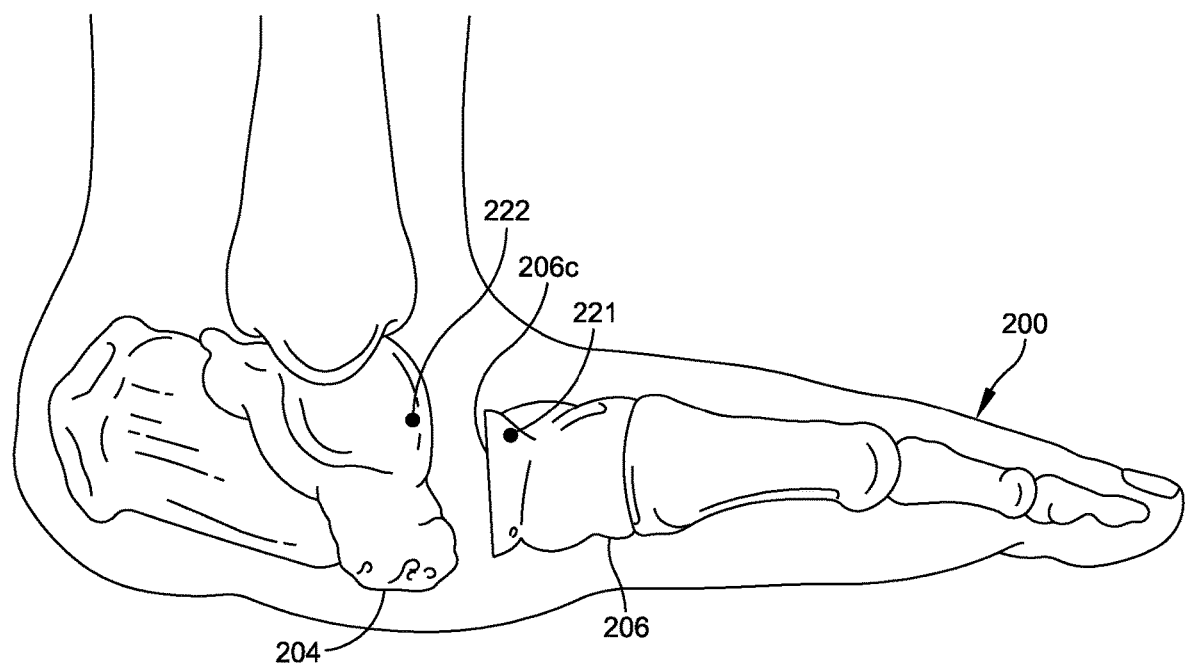
FIG. 9 shows the foot of FIG. 4 after the first planar cut is completed.

After completing the first cut, the surgeon can remove the cut guide 100. FIG. 9 shows the bone 206 after the first cut is made, and the cut guide 100 is removed.

Figure 10:
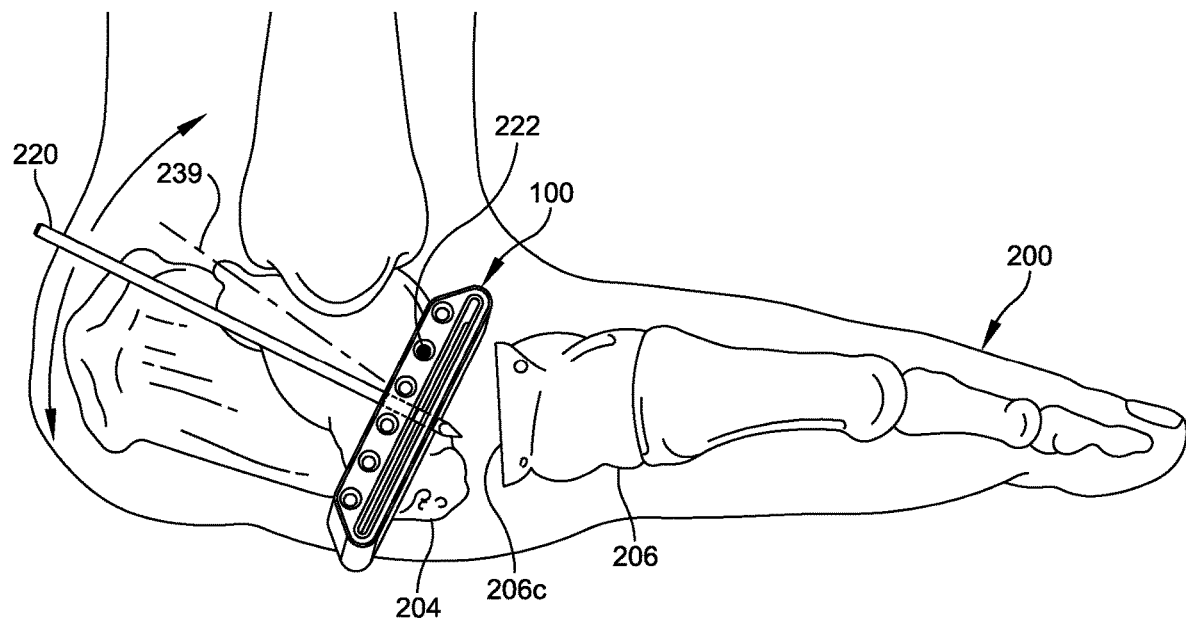
FIG. 10 shows pivoting and alignment of the cut guide of FIG. 1 on the proximal portion of the foot of FIG. 4.

The surgeon re-inserts the elongated member 220 through the alignment opening 106 extending through the cut guide 100. As shown in FIG. 10, the surgeon places one of the holes 108a-108f over the second wire 222, inserting the second wire 222 through a first hole in the cut guide 100 with the slot 104 located between the wire 222 and the diseased tissue. The surgeon can use the same holes of the cut guide for making the proximal cut, or different holes, depending on the condition of the bones.

The surgeon pivots the cut guide 100 about the second wire 222, until the first axis 109 of the cut guide 100 is aligned with the longitudinal axis 239 of the talus 204 (i.e., until the elongated member 220 is aligned with the longitudinal axis of the talus.).

Figure 11:
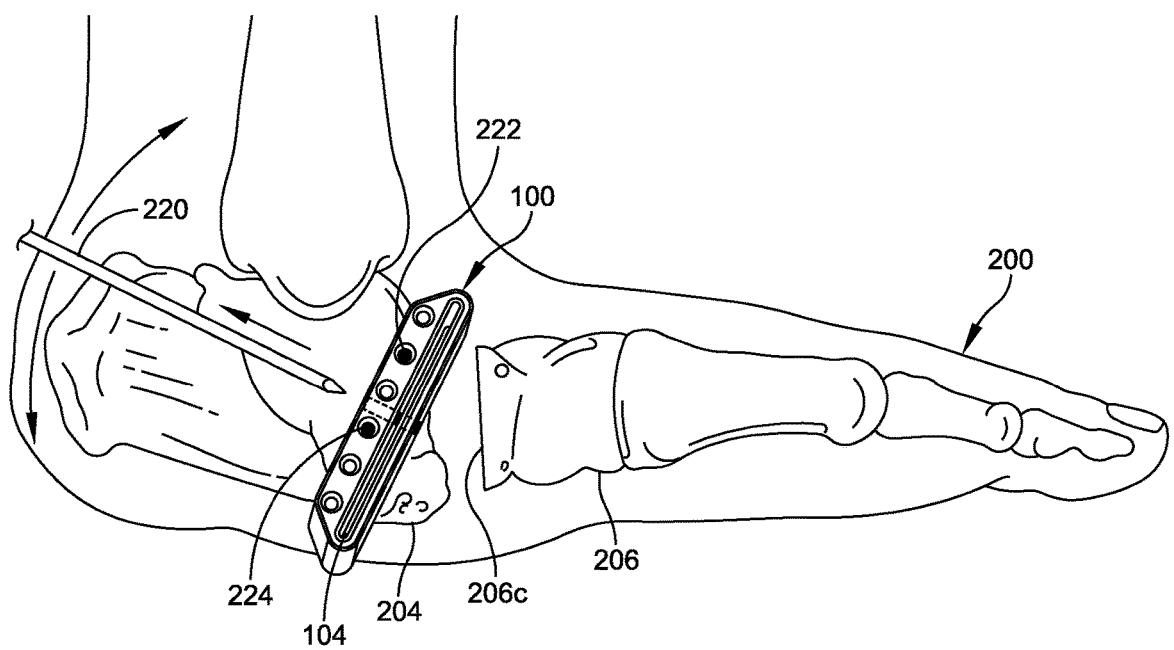
FIG. 11 shows fixation of the cut guide to the proximal portion of the foot.

As shown in FIG. 11, the surgeon inserts a fourth wire 224 through the cut guide 100, so as to fix the cut guide to the second bone while the first axis 109 of the cut guide is aligned with the longitudinal axis 239 of the talus 204. The fourth wire 224 can be inserted in any of the holes 108a-108f other than the hole through which wire 222 is inserted. The location of wire 224 is selected so that wire 224 is fixed in healthy bone. Once the fourth wire 224 is inserted and the cut guide location and orientation are fixed, the elongated member 220 can be removed as shown.

Figure 12:
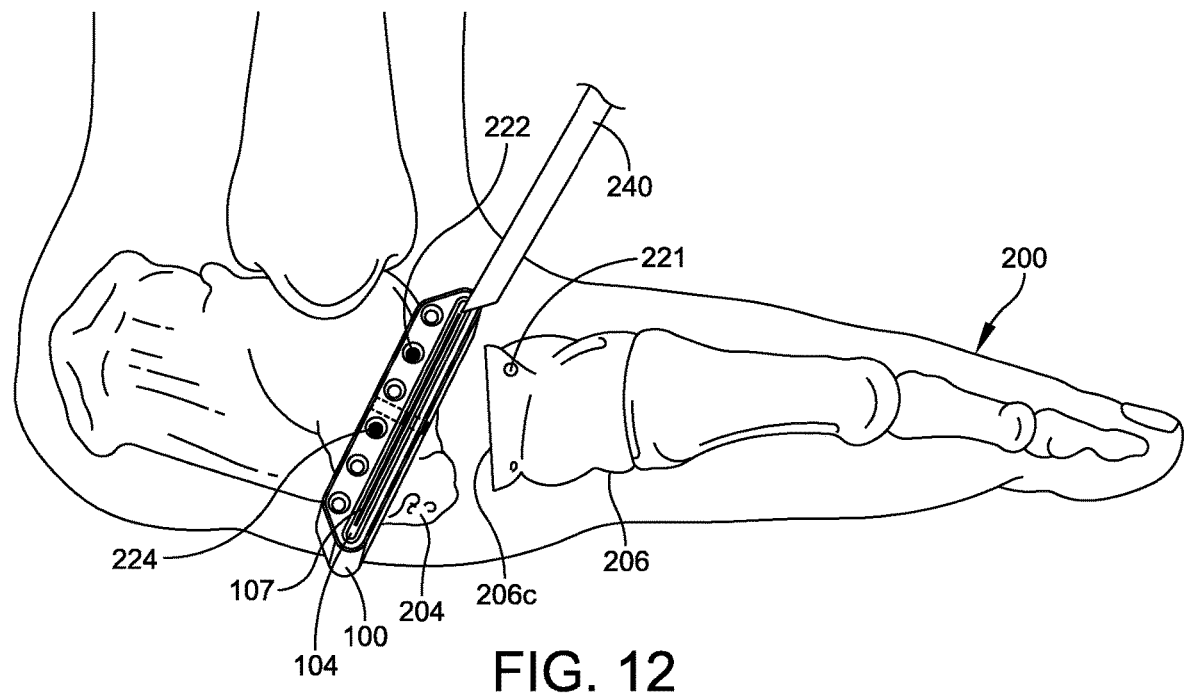
FIG. 12 shows a saw blade cutting a second bone using the cut guide.

As shown in FIG. 12, the surgeon cuts bone 204 through the slot 104 using the cutter 240 while the cut guide 100 is fixed by the second wire 222 and fourth wire 224, to form a second planar cut 107 into or through bone material. In the example of FIG. 12, the surgeon cuts completely through the bone material.

Figure 13:
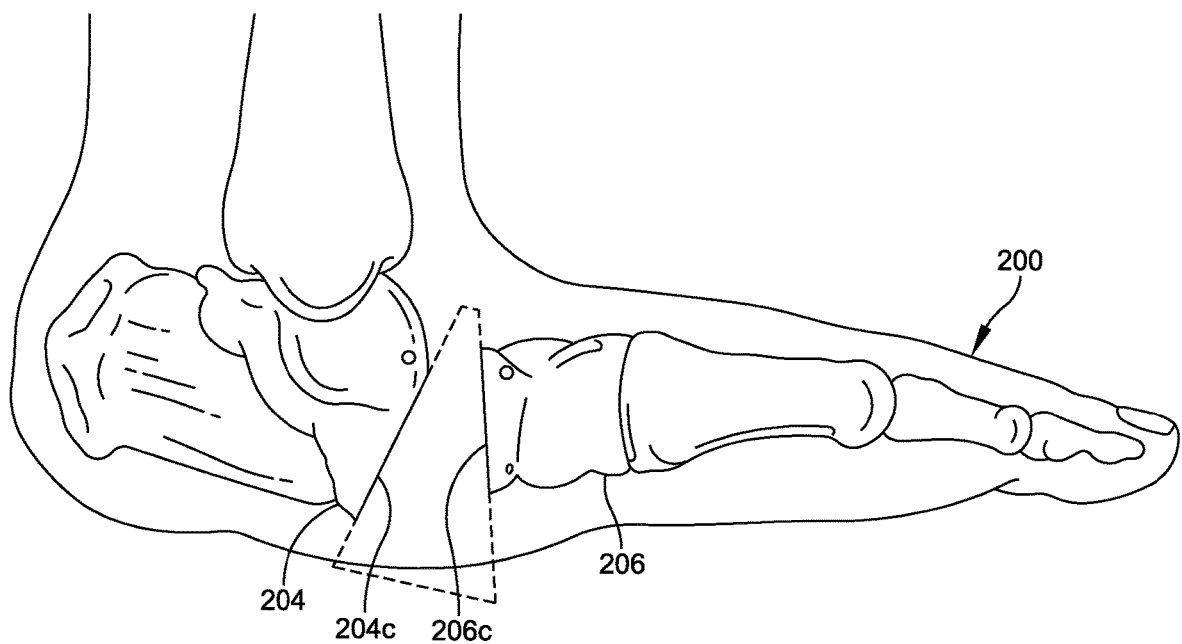
FIG. 13 shows the foot of FIG. 4 after the second planar cut is completed.

After completing the second cut, the surgeon can remove the cut guide 100. FIG. 13 shows the bones 204, 206 after the second cut is made, and the cut guide 100 is removed. The bones 204 and 206 now have planar cut surfaces 204c and 206c, respectively. The cut surface 204c is perpendicular to the longitudinal axis of the talus, and the cut surface 206c is perpendicular to the longitudinal axis of the first metatarsal 208. These are the cut orientations for reducing Meary's angle to approximately zero. FIG. 13 shows a wedge 207 in dashed lines, schematically indicating the tissue to be removed. The material removed has a triangular shape when viewed in the superior view (FIG. 7), and a trapezoidal shape when viewed in the medial view (FIG. 13). It is a complex, asymmetrical solid. The cut guide 100 and the method described herein allow the surgeon to reliably and consistently make the desired cuts on both sides of the diseased tissue.

Figure 14:
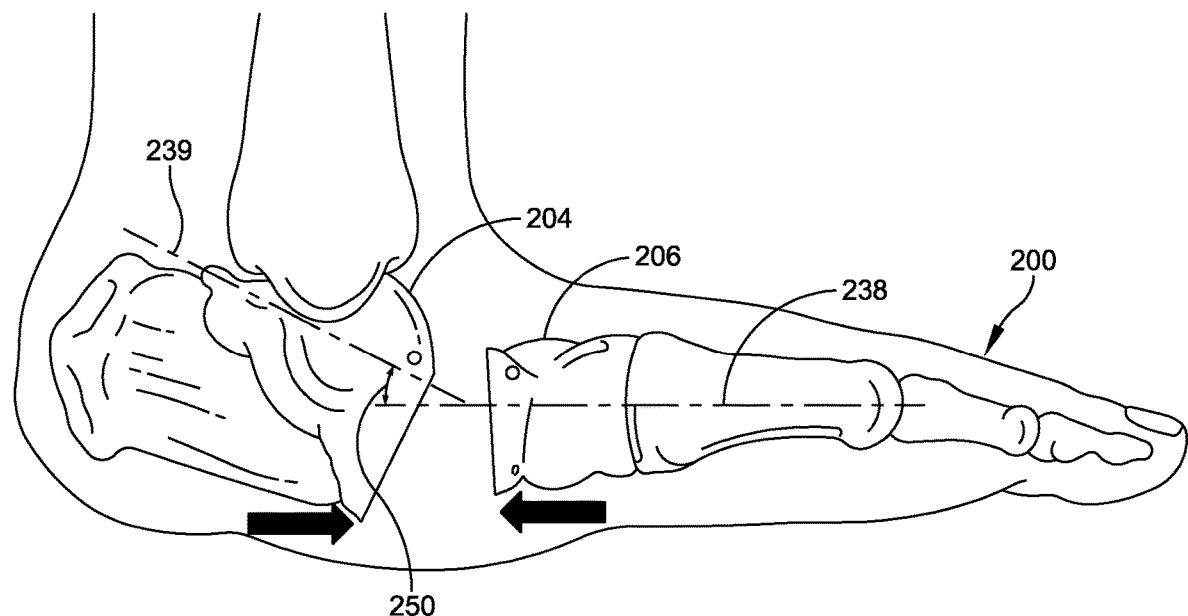
FIGS. 14 and 15 schematically show the proximal and distal cut bones of the foot being rejoined to restore a plantigrade configuration.
Figure 15:
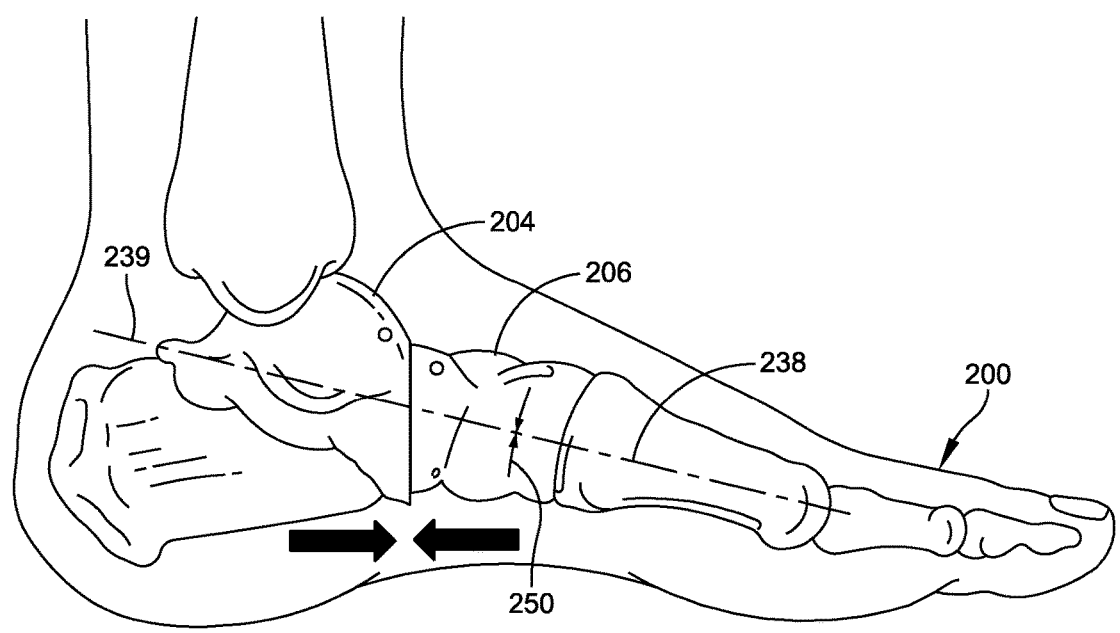

As shown in FIGS. 14 and 15, the surgeon rejoins the two cut surfaces 204c, 206c of the first and second bones 204 and 206, respectively. As shown in the example of FIG. 14, the Charcot foot 200 has a large Meary's angle 250 (between axis 238 and axis 239) of about 30 degrees. As shown in FIG. 15, when the two cut surfaces 204c, 206c are abutting, Meary's angle 250 is reduced from an angle greater than 10 degrees (e.g., 15 to 30 degrees) to approximately zero (e.g., from 0 to 4 degrees). The foot again has a plantigrade shape, and the bony prominence has been eliminated. With the arch restored, the foot is less susceptible to ulceration.

Figure 16:
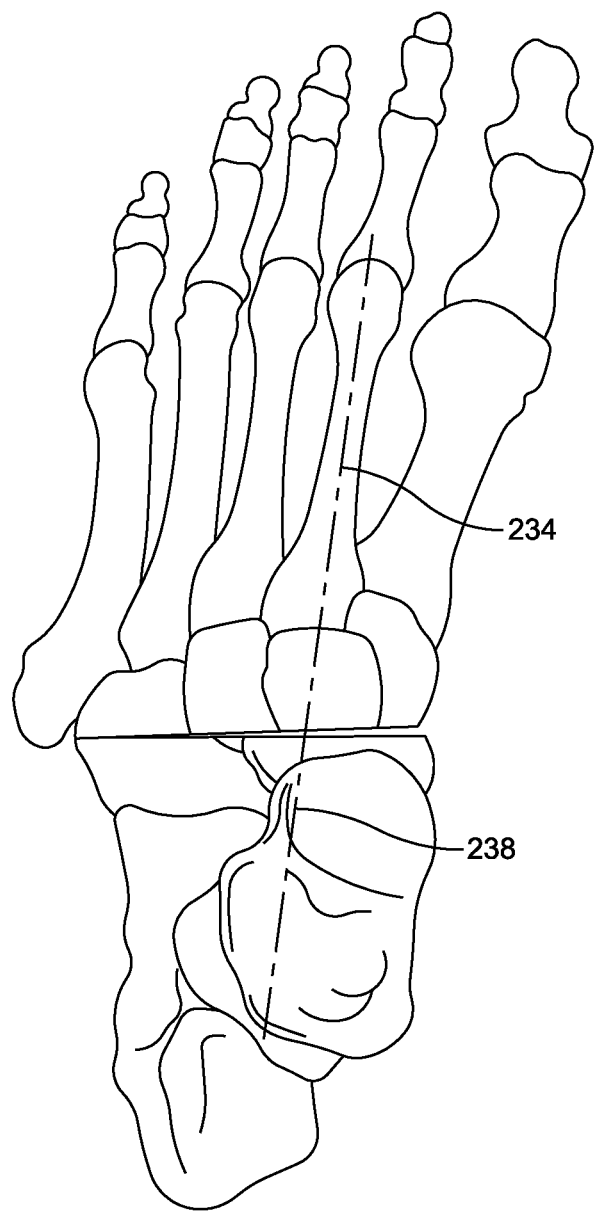
FIG. 16 is a superior view showing the rejoined bones.

FIG. 16 is a superior view of the foot after the proximal and distal portions are rejoined. The central longitudinal axis 234 of the second metatarsal 209 is approximately in line with the central longitudinal axis of the talus 204.

Figure 17:
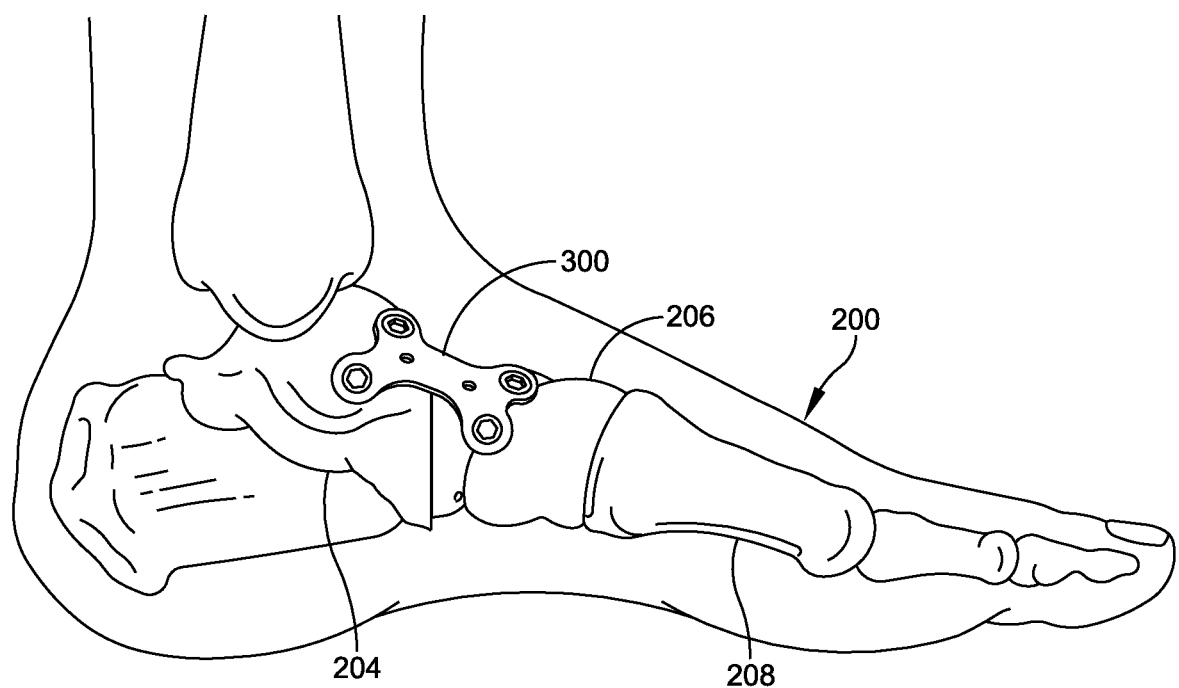
FIG. 17 shows the foot of FIG. 16 after installing a bone plate for internal fixation.

FIG. 17 shows the foot 200 after implanting a bone plate 300 to secure the proximal and distal portions of the foot together and facilitate healing. In various embodiments, a variety of internal and/or external fixation devices can be used, including one or more of the group consisting of bone plates, wires, pins, bolts, beams, a circular fixator or the like.

Figure 18:
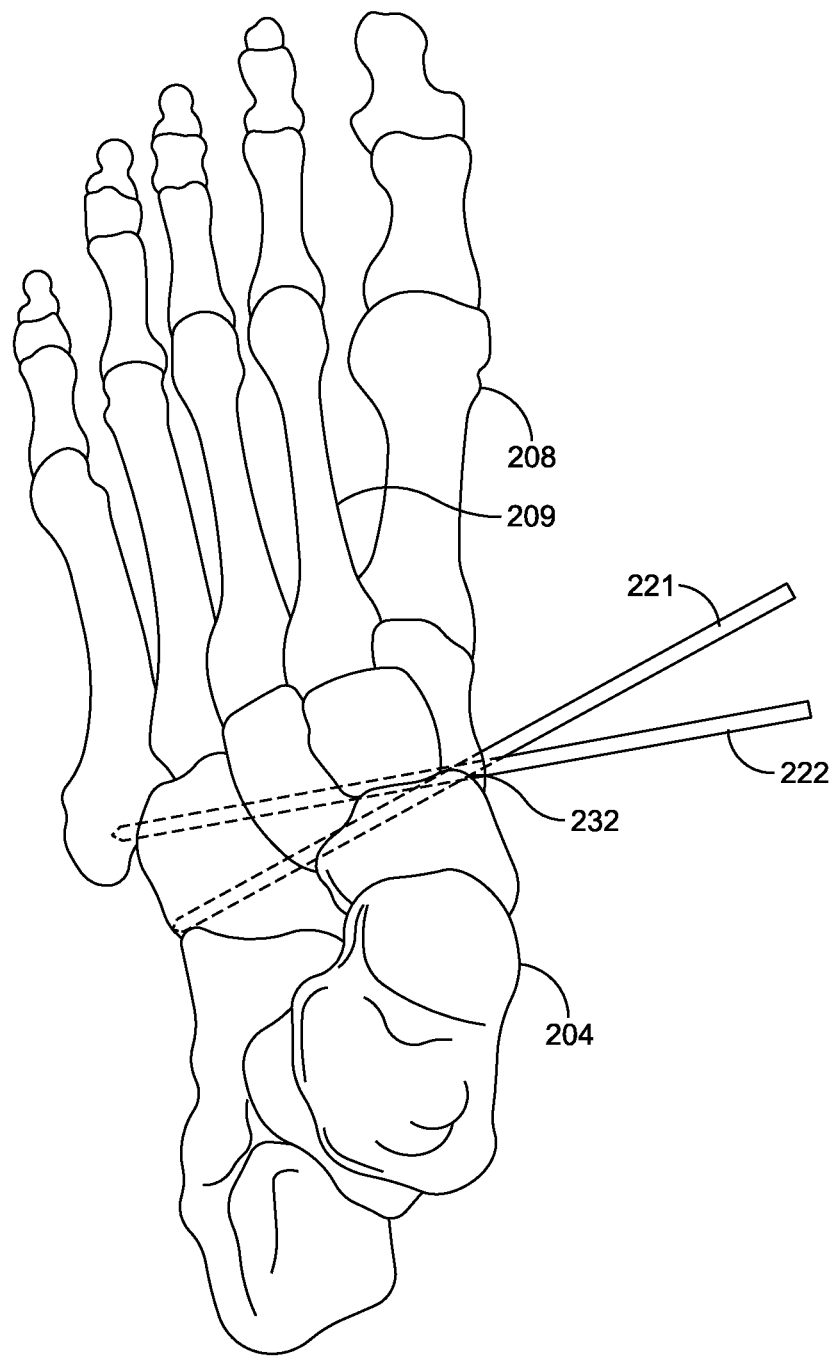
FIG. 18 is a superior view of a foot with the first and second wire inserted for performing a lateral biplanar wedge osteotomy.

FIG. 18 shows another example of locations for the first wire 221 and the second wire 222. FIG. 18 shows wire positions for a biplanar lateral wedge osteotomy using a medial approach. The wires 221 and 222 are inserted from the medial side. The apex 232 where the wires 221 and 222 cross is near the medial edge of the foot, and the wedge of tissue to be removed is on the lateral side.

Figure 19:
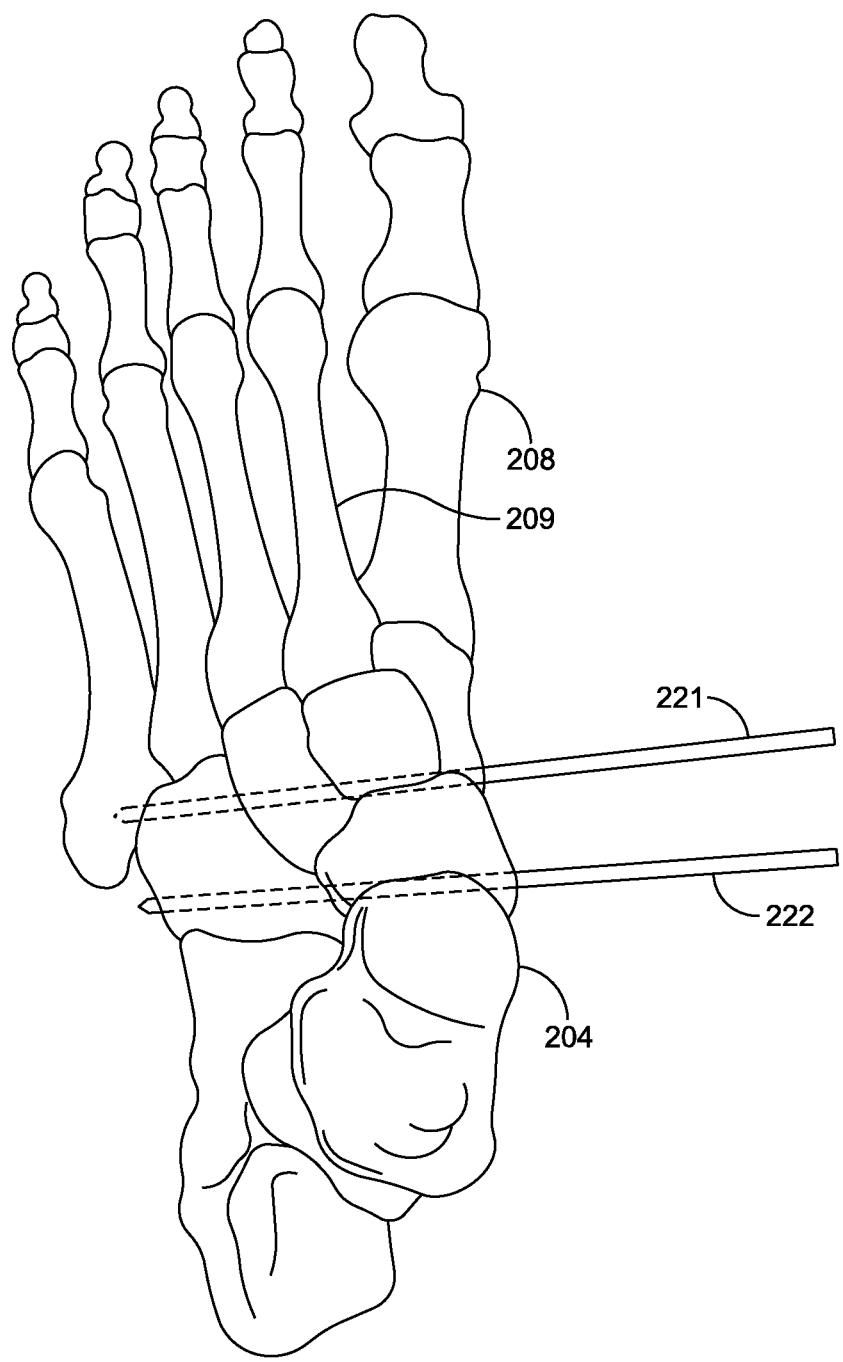
FIG. 19 is a superior view of a foot with the first and second wire inserted for removing tissue without realigning the foot.

FIG. 19 shows an example of locations for the first wire 221 and the second wire 222. FIG. 19 shows wire positions for parallel cuts using a medial approach. The apex is effectively at a very large distance past the lateral edge of the foot. The wires 221 and 222 are inserted from the medial side. This allows the surgeon to remove bad tissue and, optionally, reduce Meary's angle without realigning the metatarsals and phalanges relative to the proximal portion of the foot. For example, the surgeon may use this option to remove bad tissue if the longitudinal axis of the second metatarsal is properly in line with the longitudinal axis of the talus.

Figure 20:
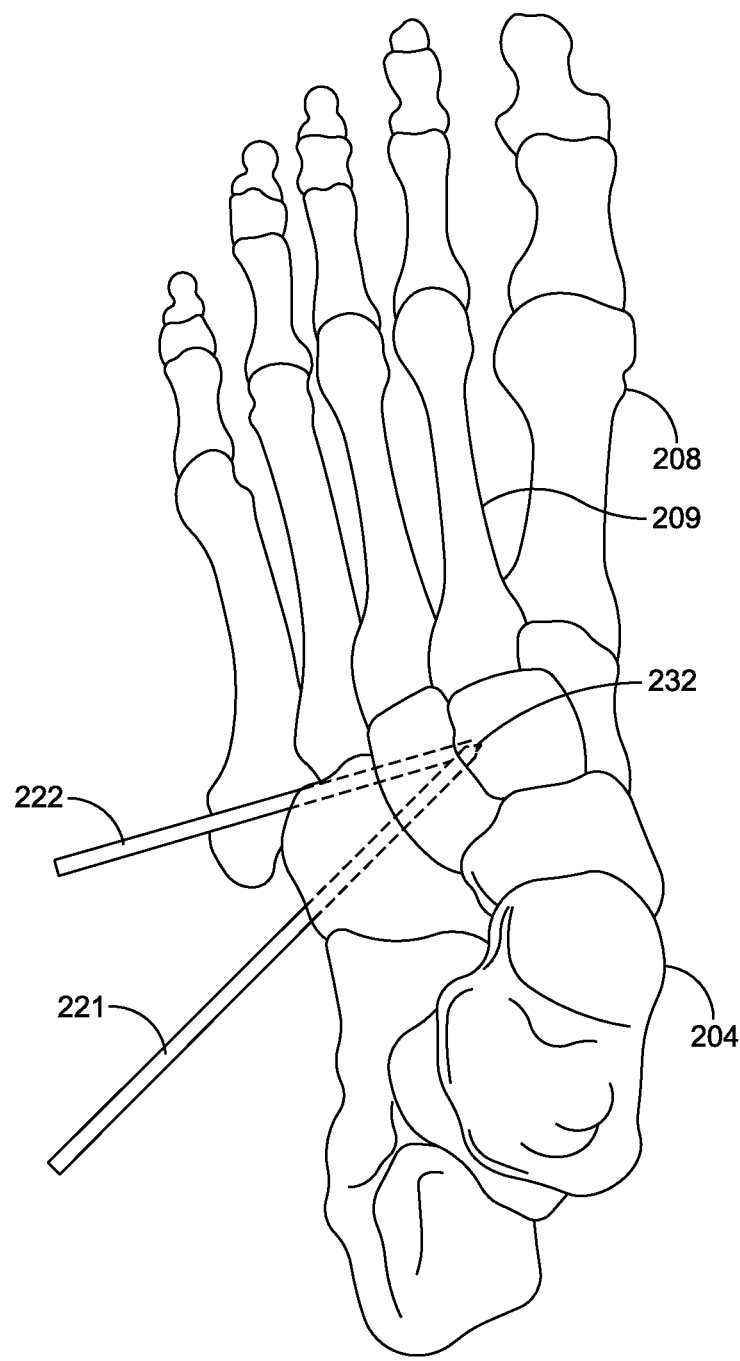
FIG. 20 is a superior view of a foot with the first and second wire inserted for removing damaged bone without realigning the bones of the foot.
Figure 21:
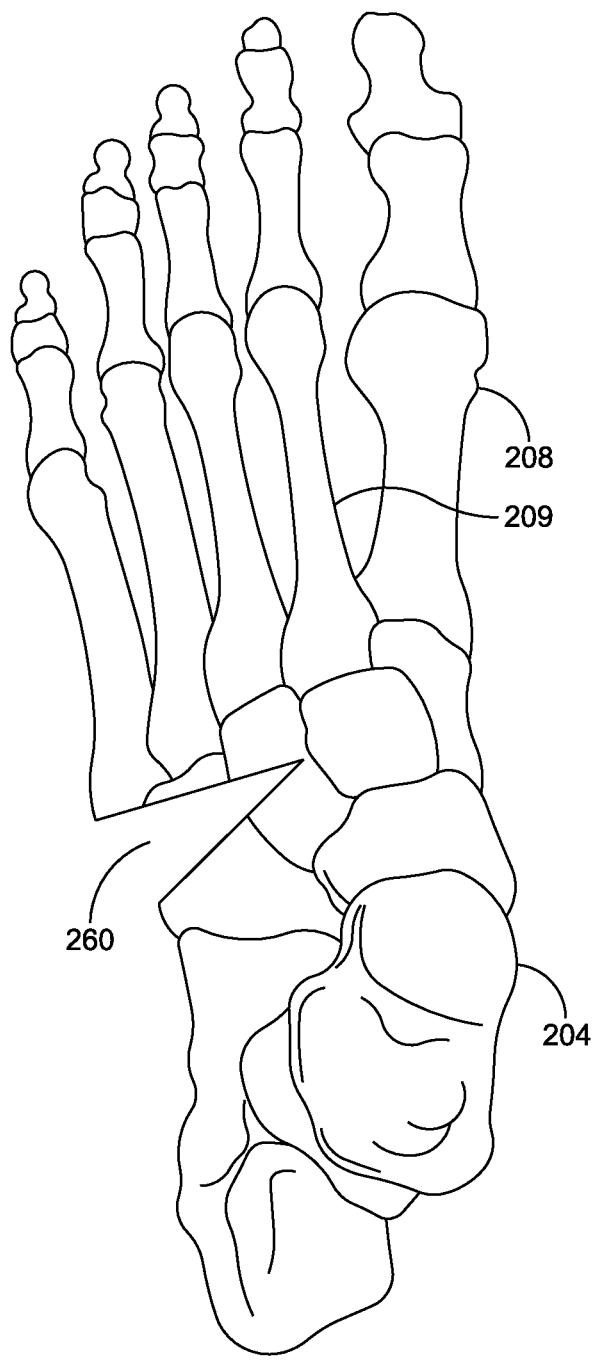
FIG. 21 shows the foot of FIG. 20 after removing a wedge of bone.
Figure 22:
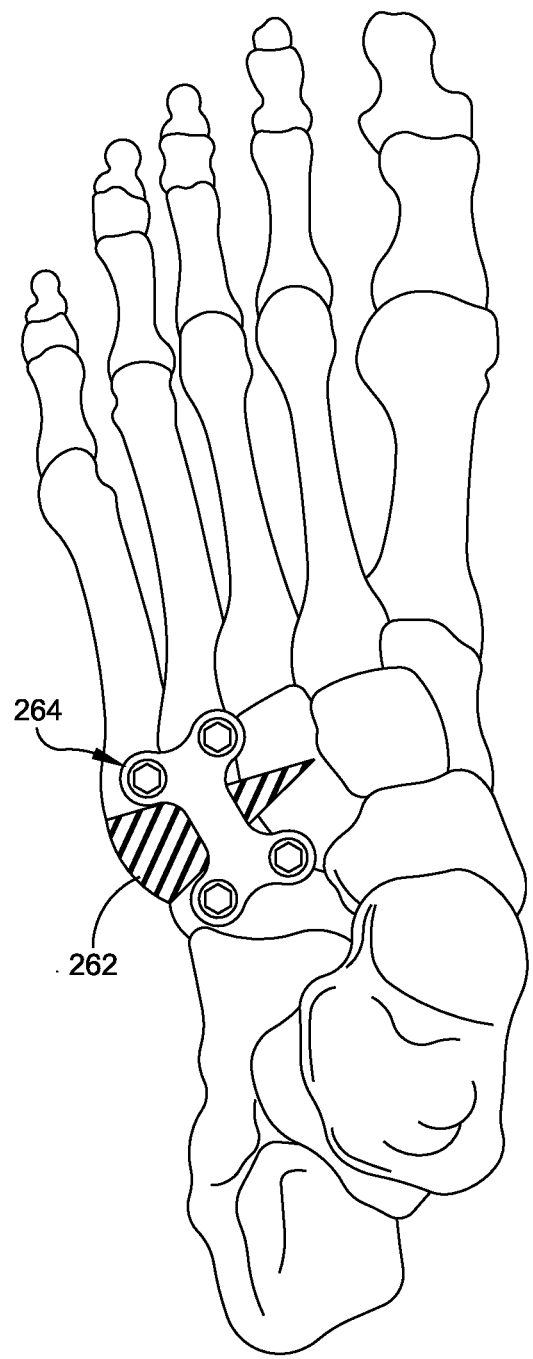
FIG. 22 shows the foot of FIG. 21 after filling the gap with autograft or suitable biocompatible material.

FIGS. 20-22 show another example of locations for the first wire 221 and the second wire 222. In this example, the steps of pivoting the cut guide around the first wire, cutting the first bone, pivoting the cut guide around the second wire, and cutting the second bone are performed while the cut guide is on a lateral side of the foot, and an apex of the cuts is in a range between the first metatarsal and the fourth metatarsal.

FIG. 20 shows wire positions for a biplanar lateral wedge osteotomy using a lateral approach. The wires 221 and 222 are inserted from the lateral side. In this example, the apex 232 where the wires 221 and 222 cross is inside the foot, and the wedge of tissue to be removed is on the lateral side. A surgeon may locate the apex 232 on the interior of the foot if the surgeon wishes to remove diseased bone without changing the alignment or Meary's angle of the foot. In this case, the surgeon can use the same cut guide 100 to guide the cutting of the bone, but it is not necessary for the cut surfaces to be perpendicular to the axes of the talus and the first metatarsal. That is, the surgeon can use the same cut guide to facilitate making straight cuts.

FIG. 21 shows the bones of the foot 200 of FIG. 20 after the wedge of tissue has been removed from the lateral side.

FIG. 22 shows the foot after the removed tissue is replaced by autograft material or an implant, such as a porous titanium matrix wedge, which is attached to the first bone and the second. Following insertion of the implant, a bone plate 264 is inserted to fixate the foot during healing. Although FIG. 22 shows a single implant, any combination of one or more of the group consisting of bone plates, wires, bolts, beams or the like can be used, with or without external fixation, such as a circular fixator. For example, the space from which bone was removed may filled with a "BIO-FOAM®" wedge, and the bones can be fixed using one or more "SALVATION®" bone plates, both sold by Wright Medical Technology, Inc. of Arlington, Tenn.

The methods described above decouple the two planar cuts of the wedge osteotomy, allowing the surgeon to consistently remove the bone material that has dropped down and is likely to cause repeated ulceration, while keeping the bone at the top of the foot. Although the examples provided above use the cut guide to perform a wedge osteotomy in the mid-foot, the cut guide can also be used for performing a wedge osteotomy in the tibia.

Although the subject matter has been described in terms of exemplary embodiments, it is not limited thereto. Rather, the appended claims should be construed broadly, to include other variants and embodiments, which may be made by those skilled in the art.

What is claimed is:

1. A method for bi-planar wedge osteotomy of a foot, comprising the steps of:
    (a) inserting a first wire at least into a first bone of the foot, so that the first wire is distal from tissue to be removed;
    (b) inserting a second wire into a second bone of the foot, so that the tissue to be removed is distal from the second wire;
    (c) pivoting a cut guide about the first wire, until a first axis of the cut guide is parallel with a longitudinal axis of a first metatarsal of the foot, the cut guide having a slot perpendicular to the first axis of the cut guide for guiding a cutter;
    (d) cutting bone through the slot while the first axis of the cut guide is aligned with the longitudinal axis of the first metatarsal;
    (e) pivoting the cut guide about the second wire, until the first axis of the cut guide is aligned with a longitudinal axis of a talus; and
    (f) cutting bone through the slot while the first axis of the cut guide is aligned with the longitudinal axis of the talus, to form a second planar cut into or through bone material.

2. The method of claim 1, wherein the cut guide has a row of holes located parallel to the slot, the method further comprising:
    placing one of the row of holes over the first wire, prior to step (c); and
    placing the same one of the row of holes or a different one of the row of holes over the second wire, prior to step (e).

3. The method of claim 2, further comprising:
    fixing the cut guide to the first bone, by inserting a third wire through another one of the row of holes before step (d); and
    fixing the cut guide to the second bone, by inserting a fourth wire through another one of the row of holes before step (f).

4. The method of claim 1, further comprising viewing a radiopaque marker of the cut guide by fluoroscopy while pivoting the cut guide about the first wire and while pivoting the cut guide about the second wire, the radiopaque marker aligned with the first axis of the cut guide.

5. The method of claim 4, wherein the radiopaque marker is an elongated metal member, and the method includes inserting the elongated metal member through an alignment opening in the cut guide before the step of viewing.

6. The method of claim 5, wherein the elongated metal member slidably or threadably engages the alignment opening.

7. The method of claim 1, wherein step (d) cuts completely through the foot along a first plane, and step (f) cuts completely through the foot along a second plane different from the first plane, further comprising attaching an implant to the first bone and the second bone.

8. The method of claim 7, wherein the foot has a Meary's angle of greater than 10 degrees before step (d), and the foot has a Meary's angle of less than 4 degrees after the step of attaching.

9. The method of claim 1, wherein step (d) cuts completely through the foot along a first plane, and step (f) cuts completely through the foot along a second plane parallel to the first plane, further comprising attaching an implant to the first bone and the second bone.

10. The method of claim 1, wherein:
- steps (c) through (f) are performed while the cut guide is on a lateral side of the foot, and
- an apex of cuts made in steps (d) and (f) is in a range between the first metatarsal and the fourth metatarsal, the method further comprising:
- removing a wedge of bone between the cuts made in steps (d) and (f); and
- inserting a wedge of a porous titanium matrix material between the cuts after the step of removing.

* * * * *